United States Patent
Miller et al.

(10) Patent No.: US 11,389,563 B2
(45) Date of Patent: Jul. 19, 2022

(54) DERMAL FILLER

(71) Applicant: Advanced Aesthetic Technologies, Inc., Brookline, MA (US)

(72) Inventors: Leonard B. Miller, Brookline, MA (US); Brian M. Kinney, Beverley Hills, CA (US)

(73) Assignee: Advanced Aesthetic Technologies, Inc., Brookline, MA (US)

( * ) Notice: Subject to any disclaimer, the term of this patent is extended or adjusted under 35 U.S.C. 154(b) by 152 days.

(21) Appl. No.: 16/621,152

(22) PCT Filed: Jun. 11, 2018

(86) PCT No.: PCT/US2018/036937
§ 371 (c)(1),
(2) Date: Dec. 10, 2019

(87) PCT Pub. No.: WO2018/231718
PCT Pub. Date: Dec. 20, 2018

(65) Prior Publication Data
US 2021/0138112 A1    May 13, 2021

Related U.S. Application Data

(60) Provisional application No. 62/518,558, filed on Jun. 12, 2017.

(51) Int. Cl.
*A61L 27/26* (2006.01)
*A61L 27/52* (2006.01)

(52) U.S. Cl.
CPC .............. *A61L 27/26* (2013.01); *A61L 27/52* (2013.01); *A61L 2430/34* (2013.01)

(58) Field of Classification Search
CPC . A61L 27/14–26; A61L 27/52; A61L 2430/34
See application file for complete search history.

(56) References Cited

U.S. PATENT DOCUMENTS

| 2010/0136070 A1 | 6/2010 | Dobak et al. |
| 2013/0203696 A1 | 8/2013 | Njikang et al. |
| 2016/0038635 A1 | 2/2016 | Matteuzzi |

FOREIGN PATENT DOCUMENTS

| CN | 1453038 A | 11/2003 |
| CN | 101134784 A | 3/2008 |
| CN | 104105474 A | 10/2014 |
| CN | 104774337 A | 7/2015 |
| DE | 19954357 C2 | 9/2002 |
| WO | 2012/131095 A1 | 10/2012 |

OTHER PUBLICATIONS

Santoro, S. et al., J. Appl. Biomater. Biomech., "Rheological properties of cross-linked hyaluronic acid dermal fillers", 2011, vol. 9, No. 2, pp. 127-136 (Year: 2011).*
Zhang, L.-M. et al., Carbohydrate Polymers, "Synthesis and characterization of a degradable composite agarose/HA hydrogel", 2012, vol. 88, pp. 1445-1452 (Year: 2012).*
Kim et al., A composite dermal filler comprising cross-linked hyaluronic acid and human collagen for tissue reconstruction. J Microbiol Biotechnol. Mar. 2015;25(3):399-406.
International Search Report and Written Opinion for Application No. PCT/US2018/036937, dated Sep. 11, 2018, 7 pages.
Kablik et al., Comparative physical properties of hyaluronic acid dermal fillers Dermatol Surg. Feb. 2009;35 Suppl 1:302-12.
Zhang, Injected Cosmetic Filler-Permeation of Hyaluronic Acid Shanghai Food and Drug Regulatory Intellegence Research. Aug. 15, 2009;4:25-28.
Chinese Office Action for Application No. 201880038213.X, dated Aug. 4, 2021, 19 pages.

* cited by examiner

*Primary Examiner* — Bahar Craigo
(74) *Attorney, Agent, or Firm* — McCarter & English, LLP; Michael J. DeGrazia; Mei Bai

(57) ABSTRACT

Embodiments of the present invention feature a dermal filler comprising a mixture of hyaluronic acid or a pharmaceutically acceptable salt thereof crosslinked with a degree of crosslinking (percent) ranging from 0.5 to 12 in an amount of 0.055 to 2.16% by weight, agarose in an amount between 0.15 to 3.5% agarose by weight and water, sodium chloride, non-gel therapeutic agents, and buffering agents to within a range of ten percent of isotonicity to create a G* value of between 50 and 400.

20 Claims, No Drawings

DERMAL FILLER

RELATED APPLICATIONS

This application is a § 371 of International Patent Application No.: PCT/US2018/036937, filed on Jun. 11, 2018, which claims priority to U.S. Provisional Application Ser. No. 62/518,558, filed on Jun. 12, 2017, The entire contents of the aforementioned applications are herein incorporated by reference.

STATEMENT REGARDING FEDERAL FUNDING

The inventions of the present application were not conceived or reduced to practice using Federal funding.

FIELD OF THE INVENTION

The inventions of the present application relate to the field of dermal fillers used for cosmetic purposes.

BACKGROUND OF THE INVENTION

As used herein, the term "dermal filler" is used to denote materials which are placed under the skin or in the dermal layers to correct or alter soft tissue. Dermal fillers are used to augment tissues which may suffer loss of volume due to lipodystophy, pathological atrophy, trauma, or as a cosmetic agent to address perceived defects and the effects of aging.

Hyaluronic acid based fillers are known in the art and comprise non-cross-linked and cross-linked forms. The cross-linked forms with greater amounts of cross-linking exhibit, generally, greater gel strength. However, greater cross-linking may be associated with greater potential for sensitivity.

There is a need for dermal fillers with modest cross linking and higher gel strength. There is a need for dermal fillers with greater longevity, structural features and lift. Such dermal fillers have utility for implants.

SUMMARY OF THE INVENTION

Embodiments of the present invention feature a composition for use as a dermal filler, a system of dermal fillers and a method of using a dermal filler. One composition of the present invention directed to a dermal filler comprises a mixture of hyaluronic acid or a pharmaceutically acceptable salt thereof crosslinked with a degree of crosslinking (percent) ranging from 0.5 to 12 in an amount of 0.055 to 2.16% by weight. The hyaluronic acid or pharmaceutically acceptable salt is in a mixture with agarose in an amount between 0.15 to 3.5% agarose by weight and water, sodium chloride, non-gel therapeutic agents, and buffering agents to within a range of ten percent of isotonicity to create a G* value of between 50 and 400.

As used herein, the term "G*" refers to the complex modulus of shear. It is a measure of resistance to deformation. As used herein, the degree of crosslinking refers to the number of moles of linked crosslinker molecules to moles of hyaluronic acid disaccharide. Non-gel therapeutic agents refers to analgesics, anti-inflammatory agents, proteins, peptides and amino acids that promote collagen growth and anti-infectives.

Compositions of the present invention feature a hyaluronic acid or pharmaceutically acceptable salt crosslinked in the presence of the agarose and/or crosslinked in the absence of the agarose. Crosslinking in the presence of agarose allows the agarose to potentially participate in the crosslinking reactions and potentially form more intimate masses with the crosslinked hyaluronic acid. Crosslinking agents comprise, by way of example, without limitation, 1,4-butandiol diglycidyl ether, divinyl sulfone, biscarbodiimide, 1,2,7,8-diepoxyoctane, hexamethylenediamine and polyethylene glycol diglycidyl ether.

A preferred composition has a G* value of greater than about 300.

A composition features agarose in a concentration of 0.15% to 3.5% by weight will have a gel structure that is approximately 10 to 70% by volume agarose where the gel comprising agarose. The remaining gel structure is 90 to 30 percent by volume hyaluronic acid or pharmaceutically acceptable salt. As used herein, the term "a gel structure having a percent volume of a component" refers to the percent of the volume which can be attributed to a component and its normal water content. Normal and customary agarose gels (without appreciable hyaluronic acid) range in concentration of 1.5% to 5.0% agarose. A composition having agarose in a concentration of 0.15% corresponds to an agarose gel in normal saline having 1.5% agarose; and, a 3.5% corresponds to a agarose gel in normal saline of 5.0% agarose.

For example, without limitation, in the event the hyaluronic acid or pharmaceutically acceptable salt has a degree of crosslinking of about 0.5 to 1.5, the concentration of the hyaluronic acid component is approximately 0.6 to 1.8%. For example, without limitation, where the hyaluronic acid or pharmaceutically acceptable salt has a degree of crosslinking of about 10 to 12, the concentration of the hyaluronic acid component is approximately 0.165 to 0.495%. As a further example, in the event the hyaluronic acid or pharmaceutically acceptable salt has a degree of crosslinking of about 6 to 8, the concentration of the hyaluronic acid component is approximately 0.72 to 2.16%.

A further composition features agarose in a concentration of 0.3% to 3.0% will have a gel structure that is approximately 20 to 60 percent by volume agarose. The remaining gel structure is 80 to 40 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 0.8 to 1.6%. For example, without limitation, where the hyaluronic acid or pharmaceutically acceptable salt has a degree of crosslinking of about 10 to 12, the concentration of the hyaluronic acid component is approximately 0.22 to 0.44%. As a further example, in the event the hyaluronic acid or pharmaceutically acceptable salt has a degree of crosslinking of about 6 to 8, the concentration of the hyaluronic acid component is approximately 0.96 to 1.92%.

A further composition features agarose in a concentration of 0.45% to 2.5% will have a gel structure that is approximately 30 to 50 percent agarose. The remaining gel structure is 70 to 50 percent hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 1.0 to 1.4%. For example, without limitation, where the hyaluronic acid or pharmaceutically acceptable salt has a degree of crosslinking of about 10 to 12, the concentration of the hyaluronic acid component is approximately 0.275 to 0.385%. As a further example, in the event the hyaluronic acid or pharmaceutically acceptable salt has a degree of crosslinking of about 6 to 8, the concentration of the hyaluronic acid component is approximately 1.2 to 1.68%.

One embodiment of the present invention features a system of dermal fillers. Each filler comprises a mixture of hyaluronic acid or a pharmaceutically acceptable salt thereof crosslinked with a degree of crosslinking (percent) ranging from 0.5 to 12 in an amount of 0.055 to 2.16% by weight. The hyaluronic acid or pharmaceutically acceptable salt is in a mixture with agarose in an amount between 0.15 to 3.5% agarose by weight and water, sodium chloride, non-gel therapeutic agents, and buffering agents to within a range of ten percent of isotonicity to create a G* value of between 50 and 400. Each filler has a different G* value.

Thus, the dermal fillers are compatible with each other and have similar properties.

For example, without limitation, one embodiment of the present invention features a dermal filler system wherein at least one first filler composition has a G* value of above about 275 and at least one second filler composition has a G* value lower than about 275. The first filler composition differs from the second composition with respect to the relative concentrations or amounts of agarose or crosslinked hyaluronic acid and/or the degree of crosslinking.

One further embodiment of the present invention features a method of effecting an aesthetic modification. The method comprises the steps of providing a composition comprising a mixture of hyaluronic acid or a pharmaceutically acceptable salt thereof crosslinked with a degree of crosslinking (percent) ranging from 0.5 to 12 in an amount of 0.055 to 2.16% by weight. The hyaluronic acid or pharmaceutically acceptable salt is in a mixture with agarose in an amount between 0.15 to 3.5% agarose by weight and water, sodium chloride, non-gel therapeutic agents, and buffering agents to within a range of ten percent of isotonicity to create a G* value of between 50 and 400.

A composition that features agarose in a concentration of 0.15% to 3.5% will have a gel structure that is approximately 10 to 70 percent by volume agarose. The remaining gel structure is 90 to 30 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 0.6 to 1.8%. For example, without limitation, where the hyaluronic acid or pharmaceutically acceptable salt has a degree of crosslinking of about 10 to 12, the concentration of the hyaluronic acid component is approximately 0.165 to 0.495%. As a further example, in the event the hyaluronic acid or pharmaceutically acceptable salt has a degree of crosslinking of about 6 to 8, the concentration of the hyaluronic acid component is approximately 0.72 to 2.16%. The method further comprises the step of injecting the dermal filler in at least one void, crease or wrinkle to create an aesthetic modification.

A further method features agarose in a concentration of 0.3% to 3.0% will have a gel structure that is approximately 20 to 60 percent by volume agarose. The remaining gel structure is 80 to 40 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 0.8 to 1.6%. For example, without limitation, where the hyaluronic acid or pharmaceutically acceptable salt has a degree of crosslinking of about 10 to 12, the concentration of the hyaluronic acid component is approximately 0.22 to 0.44%. As a further example, in the event the hyaluronic acid or pharmaceutically acceptable salt has a degree of crosslinking of about 6 to 8, the concentration of the hyaluronic acid component is approximately 0.96 to 1.92%.

A further method features agarose in a concentration of 0.45% to 2.5% will have a gel structure that is approximately 30 to 50 percent by volume agarose. The remaining gel structure is 70 to 50 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 1.0 to 1.4%. For example, without limitation, where the hyaluronic acid or pharmaceutically acceptable salt has a degree of crosslinking of about 10 to 12, the concentration of the hyaluronic acid component is approximately 0.275 to 0.385%. As a further example, in the event the hyaluronic acid or pharmaceutically acceptable salt has a degree of crosslinking of about 6 to 8, the concentration of the hyaluronic acid component is approximately 1.2 to 1.68%.

One embodiment of the method comprises the provided mixture as a hyaluronic acid or pharmaceutically acceptable salt crosslinked in the presence of the agarose or crosslinked in the absence of agarose. Crosslinking in the presence of agarose may incorporate agarose in the crosslinked structure.

One embodiment of the method features a plurality of dermal fillers including at least one first dermal filler having a first G* value and at least one second dermal filler having a second G* value. The first dermal filler and the second dermal filler differ in the amount of agarose and/or hyaluronic acid or hyaluronic acid crosslinking to allow cosmetic needs to be addressed with dermal fillers with similar antigenicity characteristics. For example, without limitation, a composition that features agarose in a concentration of 0.15% to 3.5% will have a gel structure that is approximately 10 to 70% by volume agarose and 90 to 30% by volume hyaluronic acid or pharmaceutically acceptable salt. A first filler has a first agarose concentration and the second filler has a second agarose concentration different from the first. For example, without limitation, in the event the hyaluronic acid or pharmaceutically acceptable salt has a degree of crosslinking of about 0.5 to 1.5, the concentration of the hyaluronic acid component is approximately 0.6 to 1.8%. For example, without limitation, where the hyaluronic acid or pharmaceutically acceptable salt has a degree of crosslinking of about 10 to 12, the concentration of the hyaluronic acid component is approximately 0.165 to 0.495%. As a further example, in the event the hyaluronic acid or pharmaceutically acceptable salt has a degree of crosslinking of about 6 to 8, the concentration of the hyaluronic acid component is approximately 0.72 to 2.16%. The method further comprises the step of injecting the dermal filler in at least one void, crease or wrinkle to create an aesthetic modification.

The combination of agarose and hyaluronic acid or pharmaceutically acceptable salts thereof increases the density of the filler and can be dissolved or minimized by hyaluronidase enzyme.

These and other features and advantages will be apparent to those skilled in the art upon reading the Detailed Description that follows.

DETAILED DESCRIPTION

Embodiments of the present invention will now be discussed in detail with the understanding that the present discussion is exemplary and not limiting. Embodiments of the present invention are capable of being modified and altered without departing from the teaching herein.

One embodiment of the present invention features a composition for use as a dermal filler. Dermal fillers are relatively inert materials which are administered into the deep layers of the skin to provide volume or to fill out wrinkle and creases apparent on the surface of the skin. Providing additional volume, filling out wrinkles and creases provides, for some individuals, a more youthful or athletic or attractive appearance.

One composition of the present invention directed to a dermal filler comprises a mixture of hyaluronic acid or a pharmaceutically acceptable salt thereof crosslinked with a degree of crosslinking (percent) ranging from 0.5 to 12 in an amount of 0.055 to 2.16% by weight. The hyaluronic acid or pharmaceutically acceptable salt is in a mixture with agarose in an amount between 0.15 to 3.5% agarose by weight and water, sodium chloride, non-gel therapeutic agents, and buffering agents to within a range of ten percent of isotonicity to create a G* value of between 50 and 400.

As used herein, the term "percent by weight" refers to the weight of a single component with respect to the total weight of the composition. Common gels of the hyaluronic acid or a pharmaceutically acceptable salt thereof crosslinked with a degree of crosslinking (percent) ranging from 0.5 to 12 in an amount of 0.055 to 2.16% by weight are known in the art and as described immediately above such gel would comprise approximately ninety to thirty percent of the total gel composition by volume with agarose comprising about ten to seventy percent of the total gel structure volume.

As used herein, the term "hyaluronic acid component" refers to hyaluronic acid or a pharmaceutically acceptable salt thereof. Hyaluronic acid is known in the art and comprises a unbranched glycosaminoglycan of disaccharide units. The disaccharide units are gluconic acid and N-acetyl-glucosamine.

Crosslinked hyaluronic acid components are known in the art. Hyaluronic acid is crosslinked with divinyl sulfone, 1,4-butanediol diglycidyl ether, 1,2,7,8-diepoxyoctane, hexamethylenediamine and polyethylene glycol diglycidyl ether. As used herein, the term "degree of crosslinking" refers to the ratio of crosslinking molecules to the molecules of hyaluronic acid. The value is commonly expressed as a percent.

Agarose is known in the art and comprises a linear naturally occurring polymer of alternating units of D-galactose and 3,6-anhydro-L-galactose with a glycosidic bond. In expressing the major constituents as percentages of weight, the percentages are determined by the ratio of the constituent to the total weight expressed as a percent. Normal and customary agarose gels (without appreciable hyaluronic acid) range in concentration of 1.5% to 3.5%, up to 5.0% agarose. Agarose gel concentrations by volume refer to the starting materials for the Examples. A composition having agarose in a concentration of 0.15% corresponds to a starting agarose gel having a initial concentrations in normal saline 1.5% agarose where the agarose comprised about 10% of the combined gel volume; and, a 3.5% corresponds to a agarose gel in normal saline of 5.0% agarose. A 3.5% agarose gel would form a 2.45% agarose concentration where the agarose comprised 70% of the combined gel volume.

Compositions of the present invention feature a crosslinked hyaluronic acid or pharmaceutically acceptable salt. The crosslinking of the hyaluronic acid component may be in the presence of the agarose. That is, a mixture of hyaluronic acid component and agarose is made and crosslinking agent and crosslinking reaction conditions imposed on the mixture to produce a crosslinked hyaluronic acid component that has agarose imbedded in the bonded crosslinked structure.

The crosslinking of the hyaluronic acid component may be in the absence of the agarose. Crosslinked hyaluronic acid components are readily available in the art. Such crosslinked hyaluronic acid components are mixed with agarose through agitation and mixing known in the art.

The aqueous solutions of agarose and crosslinked hyaluronic acid component are formed and combined using sterile technique. Elevated temperatures, temperature higher than about 50° C. are used to facilitate the dissolution of the components and mixing of the two components.

The mixtures are adjusted to a pH of about 7.0 and made isotonic. Those skilled in the art know how to make these adjustments with the addition of saline, water, sodium chloride, potassium chloride, sodium phosphate, sodium acid phosphate, to form phosphate buffered solutions. The term "buffering agents" encompasses such ingredients. Other ingredients such as preservatives, anesthetics, such as lidocaine, pigments and the like may also be added to the mixture of the agarose and the hyaluronic acid component.

A composition features agarose in a concentration of 0.15% to 3.5% will have a gel structure that is approximately 10 to 70 percent agarose by volume. The remaining gel structure is 90 to 30 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 0.6 to 1.8%. For example, without limitation, where the hyaluronic acid or pharmaceutically acceptable salt has a degree of crosslinking of about 10 to 12, the concentration of the hyaluronic acid component is approximately 0.165 to 0.495%. As a further example, in the event the hyaluronic acid or pharmaceutically acceptable salt has a degree of crosslinking of about 6 to 8, the concentration of the hyaluronic acid component is approximately 0.72 to 2.16%. With respect to agarose gel concentrations, the agarose gel concentration as to volume refer to the starting materials for the Examples. A composition having agarose in a concentration of 0.15% corresponds to a starting agarose gel having an initial concentration in normal saline 1.5% agarose where the agarose comprised 10% of the combined gel; and, a 3.5% corresponds to a agarose gel in normal saline of 5.0% agarose where the agarose comprised 70% of the combined gel. A 3.5% agarose gel would form a 2.45% agarose concentration where the agarose comprised 70% of the gel volume.

A further composition features agarose in a concentration of 0.3% to 3.0% will have a gel structure that is approximately 20 to 60 percent by volume agarose. The remaining gel structure is 80 to 40 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 0.8 to 1.6%. For example, without limitation, where the hyaluronic acid or pharmaceutically acceptable salt has a degree of crosslinking of about 10 to 12, the concentration of the hyaluronic acid component is approximately 0.22 to 0.44%. As a further example, in the event the hyaluronic acid or pharmaceutically acceptable salt has a degree of crosslinking of about 6 to 8, the concentration of the hyaluronic acid component is approximately 0.96 to 1.92%. With respect to agarose gel concentrations, the agarose gel concentration as to volume refers to the starting materials for the Examples. A composition having agarose in a concentration of 0.15% corresponds to a starting agarose gel having an initial concentration in normal saline 1.5% agarose forming a 10% combined gel; and, a 3.5% corresponds to a agarose gel in normal saline of 5.0% agarose forming 70% of the combined gel. A 3.5% agarose gel would form a 2.45% agarose concentration where the agarose comprised 70% of the combined gel volume.

A further composition features agarose in a concentration of 0.45% to 2.5% will have a gel structure that is approximately 30 to 50 percent by volume agarose. The remaining gel structure is 70 to 50 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 1.0 to 1.4%. For example, without limitation, where the hyaluronic acid or pharmaceutically acceptable salt has a degree of crosslinking of about 10 to 12, the concentration of the hyaluronic acid component is approximately 0.275 to 0.385%. As a further example, in the event the hyaluronic acid or pharmaceutically acceptable salt has a degree of crosslinking of about 6 to 8, the concentration of the hyaluronic acid component is approximately 1.2 to 1.68%. With respect to agarose gel concentrations, the agarose gel concentration as to volume are the starting materials for the Examples. A combined gel composition having agarose in a concentration of 0.45% corresponds to a starting agarose gel having a initial concentrations in normal saline 1.5% agarose; and, a 2.5% agarose concentration in a combined gel corresponds to an agarose gel in normal saline of 5.0% agarose forming a 50% agarose in a combined gel. A 3.5% agarose gel would form a 1.75% agarose concentration where the agarose comprised 50% of the combined gel volume.

One embodiment of the present invention features a system of dermal fillers. Each filler comprises a mixture of hyaluronic acid or a pharmaceutically acceptable salt thereof crosslinked with a degree of crosslinking (percent) ranging from 0.5 to 12 in an amount of 0.055 to 2.16% by weight. The hyaluronic acid or pharmaceutically acceptable salt is in a mixture with agarose in an amount between 0.15 to 3.5% agarose by weight and water, sodium chloride, non-gel therapeutic agents, and buffering agents to within a range of ten percent of isotonicity to create a G* value of between 50 and 400. Each filler has a different G* value.

Thus, the dermal fillers are compatible with each other and have similar properties.

For example, without limitation, one embodiment of the present invention features a dermal filler system wherein at least one first filler composition has a G* value of above about 275 and at least one second filler composition has a G* value lower than about 275. The first filler composition differs from the second composition with respect to the relative concentrations or amounts of agarose or crosslinked hyaluronic acid and/or the degree of crosslinking.

For example, without limitation, one embodiment of the present invention features a dermal filler system wherein at least one first filler composition has a G* value of above about 275 and a percentage of agarose and at least one second filler composition has a G* value lower than about 275 and a percentage of agarose lower than the first filler composition. The first filler composition differs from the second composition with respect to the relative concentrations or amounts of agarose or crosslinked hyaluronic acid.

Embodiments of the present invention will now be described as to the manner of use with respect to the method of the present invention. One further embodiment of the present invention features a method of effecting an aesthetic modification. The method comprises the steps of providing a composition comprising a mixture of hyaluronic acid or a pharmaceutically acceptable salt thereof crosslinked with a degree of crosslinking (percent) ranging from 0.5 to 12 in an amount of 0.055 to 2.16% by weight. The hyaluronic acid or pharmaceutically acceptable salt is in a mixture with agarose in an amount between 0.15 to 3.5% agarose by weight and water, sodium chloride, non-gel therapeutic agents, and buffering agents to within a range of ten percent of isotonicity to create a G* value of between 50 and 400. The composition is injected into the dermis beneath a void, wrinkle, crease or other undesired depression in the skin surface, or to provide lift, or volume, or to expand the skin to minimize creases and or wrinkles.

A composition that features agarose in a concentration of 0.15% to 3.5% will have a gel structure that is approximately 10 to 70 percent by volume agarose. The remaining gel structure is 90 to 30 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 0.6 to 1.8%. For example, without limitation, where the hyaluronic acid or pharmaceutically acceptable salt has a degree of crosslinking of about 10 to 12, the concentration of the hyaluronic acid component is approximately 0.165 to 0.495%. As a further example, in the event the hyaluronic acid or pharmaceutically acceptable salt has a degree of crosslinking of about 6 to 8, the concentration of the hyaluronic acid component is approximately 0.72 to 2.16%.

A further method features agarose in a concentration of 0.3% to 3.0% will have a gel structure that is approximately 20 to 60 percent by volume agarose. The remaining gel structure is 80 to 40 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 0.8 to 1.6%. For example, without limitation, where the hyaluronic acid or pharmaceutically acceptable salt has a degree of crosslinking of about 10 to 12, the concentration of the hyaluronic acid component is approximately 0.22 to 0.44%. As a further example, in the event the hyaluronic acid or pharmaceutically acceptable salt has a degree of crosslinking of about 6 to 8, the concentration of the hyaluronic acid component is approximately 0.96 to 1.92%.

A further method features agarose in a concentration of 0.45% to 2.5% will have a gel structure that is approximately 30 to 50 percent by volume agarose. The remaining gel structure is 70 to 50 percent by volume hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 1.0 to 1.4%. For example, without limitation, where the hyaluronic acid or pharmaceutically acceptable salt has a degree of crosslinking of about 10 to 12, the concentration of the hyaluronic acid component is approximately 0.275 to 0.385%. As a further example, in the event the hyaluronic acid or pharmaceutically acceptable salt has a degree of crosslinking of about 6 to 8, the concentration of the hyaluronic acid component is approximately 1.2 to 1.68%.

One embodiment of the method features a plurality of dermal fillers including at least one first dermal filler having a first G* value and at least one second dermal filler having a second G* value. The first dermal filler and the second dermal filler differ in the amount of agarose and/or hyaluronic acid or hyaluronic acid crosslinking to allow cosmetic needs to be addressed with dermal fillers with similar antigenicity characteristics. For example, without limitation, a composition that features agarose in a concentration of 0.15% to 3.5% will have a gel structure that is approximately 10 to 70% by volume agarose and 90 to 30% by volume hyaluronic acid or pharmaceutically acceptable salt. A first filler has a first agarose concentration and the second filler has a second agarose concentration different from the first. For example, without limitation, in the event the hyaluronic acid or pharmaceutically acceptable salt has a degree of crosslinking of about 0.5 to 1.5, the concentration of the hyaluronic acid component is approximately 0.6 to 1.8%. For example, without limitation, where the hyaluronic acid or pharmaceutically acceptable salt has a degree of crosslinking of about 10 to 12, the concentration of the hyaluronic acid component is approximately 0.165 to 0.495%. As a further example, in the event the hyaluronic acid or pharmaceutically acceptable salt has a degree of crosslinking of about 6 to 8, the concentration of the hyaluronic acid component is approximately 0.72 to 2.16%. The method further comprises the step of injecting the dermal filler in at least one void, crease or wrinkle to create an aesthetic modification.

A plurality of dermal fillers including at least one first dermal filler having a first G* value and at least one second dermal filler having a second G* value. The first dermal filler and the second dermal filler differ in the amount of agarose and allow cosmetic needs to be addressed with dermal fillers with similar antigenicity characteristics. For example, without limitation, a composition that features agarose in a concentration of 0.15% to 3.5% will have a gel structure that is approximately 10 to 70% agarose. A first filler has a first agarose concentration and the second filler has a second agarose concentration different from the first. The remaining gel structure is 90 to 30 percent hyaluronic acid or pharmaceutically acceptable salt. For example, without limitation, in the event the hyaluronic acid or pharmaceutically acceptable salt has a degree of crosslinking of about 0.5 to 1.5, the concentration of the hyaluronic acid component is approximately 0.6 to 1.8%. For example, without limitation, where the hyaluronic acid or pharmaceutically acceptable salt has a degree of crosslinking of about 10 to 12, the concentration of the hyaluronic acid component is approximately 0.165 to 0.495%. As a further example, in the event the hyaluronic acid or pharmaceutically acceptable salt has a degree of crosslinking of about 6 to 8, the concentration of the hyaluronic acid component is approximately 0.72 to 2.16%. The method further comprises the step of injecting the dermal filler in at least one void, crease or wrinkle to create an aesthetic modification.

One or more combinations of crosslinked hyaluronic acid component with agarose provides a dermal filler with high G* values of 300 or more. The high G* values allow a first filler to provide lift to the dermal features. As used herein, the term "lift" refers to structure and firmness that allow setting the dermal mass in place and holding such position over time. Thus, the filler is advantageously suited to augment cheek bone areas of the face.

A second filler having one or more crosslinked hyaluronic acid component with agarose and a low G* value, less than about 275 is used to complement the first. Such fillers are useful for expressive areas of the face which move, contract or expand.

These and other features and advantages will be apparent to those skilled in the art from the following Examples which feature methods of making dermal fillers of the present invention.

EXAMPLES

This example describes making a dermal filler comprises a mixture of hyaluronic acid or a pharmaceutically acceptable salt thereof crosslinked with a degree of crosslinking (percent) ranging from 0.5 to 12 in an amount of 0.055 to 2.16% by weight. The hyaluronic acid or pharmaceutically acceptable salt is in a mixture with agarose in an amount between 0.15 to 2.45% agarose by weight and water, sodium chloride, non-gel therapeutic agents, and buffering agents to within a range of ten percent of isotonicity to create a G* value of between 50 and 400.

This dermal filler has agarose in a concentration of 0.15% to 3.5% forming a gel structure that is approximately 10 to 70 percent agarose by volume. The remaining gel structure is 90 to 30 percent by volume hyaluronic acid or pharmaceutically acceptable salt.

A. Crosslinking of 0.5 to 1.5

Hyaluronic acid or pharmaceutically acceptable salt having a degree of crosslinking of about 0.5 to 1.5, where the desired concentration of the hyaluronic acid component is approximately 0.6 to 1.8% is combined with agarose in the following manner. Hyaluronic acid gels having such crosslinking are sold under the trademarks Restylane® (Medicis) and Perlane® (Medicis). 90 to 30 ml of hyaluronic acid gel (in buffered isotonic saline) is combined with agarose gel (in buffered isotonic saline) to make to a total volume of 100 ml (about 10 to 70 ml). Agarose gel is available in concentrations ranging from 1.5 to 3.5% by weight, sold under the trademarks Alginase® (Advanced Aesthetic Technologies Inc., Brookline Mass.). A 5.0% by weight agarose gel is made by mixing 5000 mg of agarose with 100 ml buffered isotonic saline.

The combined hyaluronic acid and agarose gels are agitated and/or mixed thoroughly.

B. Crosslinking 6-8

Hyaluronic acid or pharmaceutically acceptable salt has a degree of crosslinking of about 6 to 8, where the desired concentration of the hyaluronic acid component is approximately 0.72 to 2.16% by weight is combined with agarose in the following manner. Hyaluronic acid gels having a degree of crosslinking of about 6 to 8 are available under the trademarks Juvederm® Ultra and Ultra Plus (Allergan). Agarose gel is available in concentrations ranging from 1.5 to 3.5% by weight sold under the trademarks Alginase® (Advanced Aesthetic Technologies Inc., Brookline Mass.). A 5.0% by weight agarose gel is made by mixing 5000 mg of agarose with 100 ml buffered isotonic saline.

90 to 30 ml of hyaluronic acid gel (in buffered isotonic saline) is combined with agarose gel (in buffered isotonic saline) to a total volume of 100 ml (about 10 to 70 ml).

The combined hyaluronic acid and agarose gels are agitated and/or mixed thoroughly.

B. Crosslinking 10-12

Hyaluronic acid or pharmaceutically acceptable salt has a degree of crosslinking of about 10 to 12, where the desired concentration of the hyaluronic acid component is approximately 0.165 to 0.495% by weight is combined with agarose in the following manner. Hyaluronic acid gels having a degree of crosslinking of about 10 to 12 are available under the trademarks Prevelle® Silk (Mentor). Agarose gel is available in concentrations ranging from 1.5 to 3.5% by weight sold under the trademarks Alginase® (Advanced Aesthetic Technologies Inc., Brookline Mass.). A 5.0% by weight agarose gel is made by mixing 5000 mg of agarose with 100 ml buffered isotonic saline.

90 to 30 ml of hyaluronic acid gel (in buffered isotonic saline) is combined with agarose gel (in buffered isotonic saline) to a total volume of 100 ml (about 10 to 70 ml).

The combined hyaluronic acid and agarose gels are agitated and/or mixed thoroughly.

Dermal fillers featuring agarose have extended in vivo effectiveness and and are slowly absorbed by the body. Thus, the dermal fillers of the present invention have advantages and features which are not possible with pure hyaluronic acid products. The agarose is maintained at a level which allows ease in administering and positioning of the dermal filler mass.

Thus, embodiments of the present invention have been described in detail with the understanding that these embodiments are subject to modification and alteration and the invention should not be limited to such descriptions but should encompass the subject matter of the following claims and their equivalents.

What is claimed is:

1. A dermal filler comprising a mixture of:
   a. hyaluronic acid or a pharmaceutically acceptable salt thereof crosslinked with a degree of crosslinking ranging from 0.5 to 12 percent in an amount of 0.055 to 2.16% by weight of the dermal filler;
   b. agarose in an amount between 0.15 to 3.5% agarose by weight of the dermal filler; and
   c. water, sodium chloride, non-gel therapeutic agents, and buffering agents to within a range of ten percent of isotonicity to create a G* value of between 50 and 400.

2. The dermal filler of claim 1 wherein the hyaluronic acid or pharmaceutically acceptable salt thereof is crosslinked in the presence of the agarose.

3. The dermal filler of claim 1 wherein the hyaluronic acid or pharmaceutically accepted salt thereof is crosslinked in the absence of the agarose.

4. The dermal filler of claim 1 wherein the hyaluronic acid or a pharmaceutically acceptable salt thereof is crosslinked with a crosslinking agent selected from the group consisting of 1, 4-butanediol diglycidyl ether, divinyl sulfone, biscarbodiimide, 1,2,7,8-diepoxyoctane, hexamethylenediamine and polyethylene glycol diglycidyl ether.

5. The dermal filler of claim 1 having a G* value of greater than about 300.

6. The dermal filler of claim 1 having a gel structure that is made of approximately 10 to 70% by volume of the agarose and 90 to 30 percent by volume of the hyaluronic acid or pharmaceutically acceptable salt thereof.

7. The dermal filler of claim 1 wherein the degree of crosslinking is about 0.5 to 1.5 percent and the concentration of the hyaluronic acid or pharmaceutically acceptable salt thereof is approximately 0.6 to 1.8% by weight of the dermal filler.

8. The dermal filler of claim 1 wherein the degree of crosslinking is about 10 to 12 percent and the concentration of the hyaluronic acid or pharmaceutically acceptable salt thereof is approximately 0.165 to 0.495% by weight of the dermal filler.

9. The dermal filler of claim 1 wherein the degree of crosslinking is about 6 to 8 percent and the concentration of the hyaluronic acid or pharmaceutically acceptable salt thereof is approximately 0.72 to 2.16% by weight of the dermal filler.

10. The dermal filler of claim 1 having a gel structure that is made of approximately 20 to 60 percent by volume of the agarose wherein said agarose is present in a concentration of 0.3% to 3.0% by weight of the dermal filler and 80 to 40 percent by volume of the hyaluronic acid or pharmaceutically acceptable salt thereof.

11. The dermal filler of claim 10 wherein said hyaluronic acid or pharmaceutically acceptable salt thereof has a degree of crosslinking of about 0.5 to 1.5 percent and the concentration of the hyaluronic acid or pharmaceutically acceptable salt thereof is approximately 0.8 to 1.6% by weight of the dermal filler.

12. The dermal filler of claim 10 wherein said hyaluronic acid or pharmaceutically acceptable salt thereof has a degree of crosslinking of about 10 to 12 percent and the concentration of the hyaluronic acid or pharmaceutically acceptable salt thereof is approximately 0.22 to 0.44% by weight of the dermal filler.

13. The dermal filler of claim 10 wherein the hyaluronic acid or pharmaceutically acceptable salt thereof has a degree of crosslinking of about 6 to 8 percent and the concentration of the hyaluronic acid or pharmaceutically acceptable salt thereof is approximately 0.96 to 1.92% by weight of the dermal filler.

14. The dermal filler of claim 1 having a gel structure that is approximately 30 to 50 percent agarose by volume wherein said agarose has a concentration of 0.45% to 2.5% by weight of the dermal filler and 70 to 50 percent by volume of the hyaluronic acid or pharmaceutically acceptable salt thereof.

15. The dermal filler of claim 14 wherein said hyaluronic acid or pharmaceutically acceptable salt thereof has a degree of crosslinking of about 0.5 to 1.5 percent and the concentration of the hyaluronic acid component is approximately 1.0 to 1.4% by weight of the dermal filler.

16. The dermal filler of claim 14 wherein said hyaluronic acid or pharmaceutically acceptable salt thereof has a degree of crosslinking of about 10 to 12 percent and the concentration of the hyaluronic acid or pharmaceutically acceptable salt thereof is approximately 0.275 to 0.385% by weight of the dermal filler.

17. The dermal filler of claim 14 wherein said hyaluronic acid or pharmaceutically acceptable salt thereof has a degree of crosslinking of about 6 to 8 percent and the concentration of the hyaluronic acid or pharmaceutically acceptable salt thereof is approximately 1.2 to 1.68% by weight of the dermal filler.

18. A system of dermal fillers comprising at least one first dermal filler and one second dermal filler, said first dermal filler and said second dermal filler each being independently selected from the dermal filler according to claim 1; wherein said first filler has a first G* and said second dermal filler has a second G* value which is different from said first G* value.

19. The system of claim 18 wherein said first dermal filler differs from the second dermal filler with respect to at least one of the relative concentrations or amounts of agarose or crosslinked hyaluronic acid and/or the degree of crosslinking.

20. A method of effecting an aesthetic modification comprises the steps of:
   a. providing the dermal filler according to claim 1; and b. placing said dermal filler to fill a void, expand a skin surface, add volume and/or diminish the appearance of wrinkles and creases.

\* \* \* \* \*

UNITED STATES PATENT AND TRADEMARK OFFICE
CERTIFICATE OF CORRECTION

Page 1 of 1

PATENT NO. : 11,389,563 B2
APPLICATION NO. : 16/621152
DATED : July 19, 2022
INVENTOR(S) : Miller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 76 days.

Signed and Sealed this
Eleventh Day of February, 2025

Coke Morgan Stewart
*Acting Director of the United States Patent and Trademark Office*